United States Patent
Ray et al.

(10) Patent No.: US 12,281,297 B2
(45) Date of Patent: *Apr. 22, 2025

(54) SYSTEMS AND METHODS FOR PRODUCING BIOPRODUCTS

(71) Applicant: EMD Millipore Corporation, Burlington, MA (US)

(72) Inventors: Roderick J. Ray, Bend, OR (US); Adam S. Carroll, Bend, OR (US); Brandon J. Downey, Bend, OR (US); Lisa J. Graham, Bend, OR (US)

(73) Assignee: EMD Millipore Corporation, Burlington, MA (US)

( * ) Notice: Subject to any disclaimer, the term of this patent is extended or adjusted under 35 U.S.C. 154(b) by 1196 days.

This patent is subject to a terminal disclaimer.

(21) Appl. No.: 17/086,249

(22) Filed: Oct. 30, 2020

(65) Prior Publication Data
US 2021/0047606 A1    Feb. 18, 2021

Related U.S. Application Data

(63) Continuation of application No. 16/557,913, filed on Aug. 30, 2019, now Pat. No. 10,836,991, which is a continuation of application No. 14/353,753, filed as application No. PCT/US2012/061706 on Oct. 24, 2012, now Pat. No. 10,421,939.

(60) Provisional application No. 61/603,809, filed on Feb. 27, 2012, provisional application No. 61/584,192, filed on Jan. 6, 2012, provisional application No. 61/550,823, filed on Oct. 24, 2011.

(51) Int. Cl.
| | |
|---|---|
| C12M 1/36 | (2006.01) |
| C12M 1/00 | (2006.01) |
| C12M 1/12 | (2006.01) |
| C12M 1/26 | (2006.01) |
| C12M 1/34 | (2006.01) |
| C12Q 3/00 | (2006.01) |
| G01N 33/48 | (2006.01) |

(52) U.S. Cl.
CPC ............ *C12M 41/48* (2013.01); *C12M 29/18* (2013.01); *C12M 33/04* (2013.01); *C12M 37/00* (2013.01); *C12M 41/32* (2013.01); *C12Q 3/00* (2013.01); *G01N 33/48* (2013.01)

(58) Field of Classification Search
CPC ...... C12M 41/48; C12M 29/18; C12M 33/04; C12M 37/00; C12M 41/32; C12Q 3/00; G01N 33/48
See application file for complete search history.

(56) References Cited

U.S. PATENT DOCUMENTS

| | | |
|---|---|---|
| 1,605,824 A | 11/1926 | Erickson |
| 2,835,598 A | 5/1958 | Kolner |
| 3,379,216 A | 4/1968 | Mercier |
| 3,713,988 A | 1/1973 | Dawson et al. |
| 3,741,687 A | 6/1973 | Nystroem |
| 3,771,562 A | 11/1973 | Curran |
| 3,807,906 A | 4/1974 | Breit |
| 4,347,877 A | 9/1982 | Hoiss |
| 4,548,088 A | 10/1985 | Hood, Jr. |
| 4,889,812 A | 12/1989 | Guinn et al. |
| 4,918,019 A | 4/1990 | Guinn |
| 5,075,905 A | 12/1991 | Rutherford |
| 5,131,226 A | 7/1992 | Hendry |
| 5,296,197 A | 3/1994 | Newberg et al. |
| 5,630,935 A | 5/1997 | Treu |
| 5,948,998 A | 9/1999 | Witte |
| 6,085,602 A | 7/2000 | Schorn et al. |
| 6,133,022 A | 10/2000 | Newberg |
| 6,423,548 B1 | 7/2002 | Newburg et al. |
| 6,491,283 B2 | 12/2002 | Newberg |
| 6,516,677 B1 | 2/2003 | Suter |
| 6,637,277 B2 | 10/2003 | Gamache |
| 6,821,773 B1 | 11/2004 | Newberg |
| 7,192,003 B2 | 3/2007 | Hoobyar et al. |
| 7,389,792 B2 | 6/2008 | Newberg |
| 7,601,545 B2 | 10/2009 | Barringer, Jr. |
| 7,955,843 B2 | 6/2011 | Barringer, Jr. |
| 8,549,934 B2 | 10/2013 | Biksacky |
| 9,322,749 B2 | 4/2016 | Newbold et al. |

(Continued)

FOREIGN PATENT DOCUMENTS

| | | |
|---|---|---|
| FR | 2617286 A1 | 12/1988 |
| WO | WO 2006/086489 | 8/2006 |

(Continued)

OTHER PUBLICATIONS

Swiech, Kamilla et al. "Human cells: new platform for recombinant therapeutic protein production." Protein expression and purification vol. 84, 1 (2012): 147-53. doi:10.1016/j.pep.2012.04.023 (Year: 2012).*
Daken Stainless Products: "Keofitt W15 Sample Valves", Retrieved from Internet URL <http://www.keofitt-uk.com/865541.htm>, 3 Pages.
Final Office Action Received for U.S. Appl. No. 14/353,753, mailing date Feb. 8, 2019, 7 Pages.
Final Office Action Received for U.S. Appl. No. 14/353,753, mailing date Jan. 11, 2018, 10 Pages.
Final Office Action Received for U.S. Appl. No. 14/353,753, mailing date Sep. 9, 2016, 11 Pages.

(Continued)

*Primary Examiner* — Elizabeth C. Kemmerer
*Assistant Examiner* — Mckenzie A Dunn
(74) *Attorney, Agent, or Firm* — EMD Millipore Corporation

(57) ABSTRACT

The present disclosure is directed to systems and methods for sampling and/or controlling the productivity of a bioreactor. The system and methods can include a vessel capable of providing an environment suitable for containing whole broth that can produce the bioproduct, wherein the whole broth contains media and at least one undissolved species, an automated sampling system, a first analytical instrument, and a control system.

18 Claims, 16 Drawing Sheets

(56) References Cited

U.S. PATENT DOCUMENTS

| | | | |
|---|---|---|---|
| 9,499,782 B2 | 11/2016 | Newbold et al. |
| 10,421,939 B2 | 9/2019 | Ray et al. |
| 10,836,991 B2 | 11/2020 | Ray et al. |
| 2002/0036017 A1 | 3/2002 | Leys et al. |
| 2004/0259241 A1 | 12/2004 | Barringer |
| 2005/0158701 A1 | 7/2005 | West |
| 2005/0187532 A1 | 8/2005 | Thurau et al. |
| 2007/0039653 A1 | 2/2007 | Maggard |
| 2007/0128087 A1 | 6/2007 | Cannizzaro et al. |
| 2007/0131289 A1 | 6/2007 | Pataki |
| 2008/0032380 A1 | 2/2008 | Kleis et al. |
| 2008/0134804 A1 | 6/2008 | Maeda et al. |
| 2008/0289437 A1 | 11/2008 | Saegusa |
| 2008/0308484 A1 | 12/2008 | Deb et al. |
| 2008/0314450 A1 | 12/2008 | Hawker |
| 2009/0038419 A1 | 2/2009 | Hiller et al. |
| 2009/0068032 A1 | 3/2009 | Furey |
| 2009/0178495 A1 | 7/2009 | Steigmiller et al. |
| 2009/0199904 A1 | 8/2009 | Babbitt et al. |
| 2010/0043883 A1 | 2/2010 | Yu et al. |
| 2010/0047122 A1 | 2/2010 | Barringer, Jr. |
| 2010/0102008 A1 | 4/2010 | Hedberg |
| 2010/0236340 A1 | 9/2010 | Lee et al. |
| 2011/0236990 A1 | 9/2011 | Mizutani et al. |
| 2014/0087413 A1 | 3/2014 | Newbold et al. |
| 2014/0295532 A1 | 10/2014 | Ray et al. |
| 2020/0017818 A1 | 1/2020 | Ray et al. |

FOREIGN PATENT DOCUMENTS

| | | | |
|---|---|---|---|
| WO | WO 2011/038008 | | 3/2011 |
| WO | 2013/063128 A1 | | 5/2013 |

OTHER PUBLICATIONS

Non Final Office Action Received for U.S. Appl. No. 14/353,753, mailing date Jan. 22, 2016, 10 Pages.
Non Final Office Action Received for U.S. Appl. No. 14/353,753, mailing date Jun. 20, 2018, 9 Pages.
Non Final Office Action Received for U.S. Appl. No. 14/353,753, mailing date Jun. 28, 2017, 10 Pages.
Notice of Allowance received for U.S. Appl. No. 14/353,753, mailing date May 14, 2019, 11 Pages.
Non Final Office Action Received for U.S. Appl. No. 16/557,913, mailing date Apr. 3, 2020, 9 Pages.
Notice of Allowance received for U.S. Appl. No. 16/557,913, mailing date Jul. 14, 2020, 9 Pages.
Benz, G. T.,"Bioreactor design for chemical engineers", Chemical Engineer Progress, vol. 107, Aug. 2011, pp. 21-26.
International Preliminary Report on Patentability received for PCT Application No. PCT/US2012/061706 mailing date May 8, 2014, 8 Pages.
International Search Report and Written Opinion received for PCT Application No. PCT/US2012/061706, mailing date Jan. 4, 2013, 9 Pages.
Benz. "Bioreactor Designs for Chemical Engeneers" *Chem. Eng. Progress* 107.8 (2011): 21-26.
Daken Stainless Products: "Keofitt W15 Sample Valves", (Jan. 1, 2005), Available at http://www.keofitt-uk.com/865541.htm [last accessed Oct. 19, 2015].

* cited by examiner

SYSTEMS AND METHODS FOR PRODUCING BIOPRODUCTS

CROSS REFERENCE TO RELATED APPLICATIONS

This application is a continuation of U.S. patent application Ser. No. 16/557,913, filed Aug. 30, 2019, which is a continuation of U.S. patent application Ser. No. 14/353,753, filed Apr. 23, 2014, now U.S. Pat. No. 10,421,939, which is the U.S. National Stage of International Application No. PCT/US2012/061706, filed Oct. 24, 2012, which was published in English under PCT Article 21(2), which in turn claims the benefit of U.S. Provisional Application No. 61/550,823, filed Oct. 24, 2011, U.S. Provisional Application No. 61/584,192, filed Jan. 6, 2012, and U.S. Provisional Application No. 61/603,809, filed Feb. 27, 2012. The prior applications are incorporated herein by reference in their entirety.

FIELD

The present disclosure is directed to systems and methods for sampling and/or controlling the productivity of a bioreactor.

BACKGROUND

Bioreactors and some chemical reactors are often isolated from the environment for many reasons, including for maintaining sterility, to prevent contamination, or for operator or environmental safety. Obtaining samples from such reactors can be difficult because of these needs for isolation. However, often the conditions in the reactor cannot be properly controlled without measuring properties within the reactor. Although some methods exist for determining or estimating the conditions in the reactor, such conventional methods are generally not able to utilize the information obtained to alter and/or control the biologically and/or chemically active environments to improve the conditions and product yield of the systems. Accordingly, systems and methods that provide sampling and control of reactors or other systems would be desirable.

SUMMARY

In one embodiment, a system for making a bioproduct includes a vessel capable of providing an aseptic environment suitable for containing whole broth that can produce the bioproduct. The whole broth contains media and at least one undissolved species. The system also contains an aseptic sampling system operably connected to the vessel and capable of extracting a sample from the vessel. The system also includes at least one analytical instrument operably connected to the sampling system, the analytical instrument being configured to measure at least one property of the whole broth in the vessel and generating at least one signal in response thereto. A control system is provided that in response to the at least one signal generates at least one output signal capable of controlling at least one device that is configured to alter at least one property of the whole broth within the vessel.

In one embodiment, the system further comprises a second analytical instrument operably connected to the vessel, the second analytical instrument being configured to measure at least one property of the whole broth in the vessel and generating at least one second signal which is sent to the control system.

In some embodiments, the bioproduct is selected from foods, beverages, biofuels, bioenergy, bio-based ethanol, biodiesel, bio-based adhesives, biochemicals, biotherapeutics, biodegradable plastics, and mixtures thereof. In other embodiments, the bioproduct is a biotherapeutic. In still other embodiments, the bioproduct is a biotherapeutic selected from pharmaceuticals, therapeutic proteins, protein fragments, antibodies, vaccines, and mixtures thereof.

In some embodiments, the vessel is selected from anaerobic fermenters, aerobic fermenters, stirred-tank reactors, adherent bioreactors, wave-type bioreactors, and disposable bioreactors.

In some embodiments, the undissolved species is selected from live cells, dead cells, cell fragments, solid substrates having cells adhered thereto, particles, and mixtures thereof. In other embodiments, the undissolved species is selected from bacteria, yeast, mammalian cells, and e-coli cells.

In some embodiments, the at least one property of the whole broth is selected from media-level properties and cell-level properties. In other embodiments, the at least one property of the whole broth is selected from pH, dissolved oxygen, osmolality, nutrient concentrations, ammonia/ammonium, lactate/lactic acid, pCO2, electrolytes (such as K+, Ca++, and/or Na+), amino acids, NAD/NADH, impurities, purity, phenotypes, metabolic states, cell health, cell cycle, cell state, cell number, and viable cell volume.

In some embodiments, the at least one analytical instrument is selected from pH probes, dissolved oxygen meters, ion-selective electrodes, osmometry, high-performance liquid chromatography, ultra performance liquid chromatography, gas chromatography, ion chromatography, conductivity, Raman spectroscopy, near infrared spectroscopy, dielectric spectroscopy, fluorometry, ultraviolet/visible spectroscopy, capacitance probes, luminescence, redox probes, flow cytometry, hemacytometry, electro-rotation, electrophoresis, dielectrophoresis, and mixtures thereof.

In some embodiments, the device that is configured to alter at least one property of the whole broth is selected from mixing/agitation systems, temperature-control systems, gas pumps, nutrient pumps, product removal systems, impurity removal systems, pH adjustment systems, and mixtures thereof.

In some embodiments, the aseptic sampling system is an automatic aseptic sampling system comprises (a) a sanitizing fluid inlet valve operable between an open position and a closed position; (b) a gas inlet valve operable between an open position and a closed position; (c) a sample collection valve operable between an open position and a closed position; (d) a first outlet valve operable between an open position and a closed position; (e) a variable volume reservoir; and (f) a fluid flow path interconnecting (a)-(e), wherein when (a), (b), and (d) are in the closed position, (c) can be in the open position to withdraw a sample from the enclosed container into the reservoir along a first portion of the fluid flow path, wherein when (a), (b), and (c) are in the closed position, the sample can be discharged from the reservoir along a second portion of the fluid flow path through (d), and wherein when (a) is in the open position and (b) and (c) are in the closed position, a sanitizing fluid can be introduced into the fluid flow path through (a) to sanitize at least the first portion of the fluid flow path.

In some embodiments, the aseptic sample system extracts a sample from the vessel at least once every 8 hours of operation of a bioreactor or other such system, at least once every 6 hours of operation, at least once every 4 hours of operation, at least once every 2 hours of operation, at least once every 1 hour of operation, at least once every 0.5 hours of operation, at least once every 20 minutes of operation, at least once every 15 minutes of operation, at least once every 10 minutes of operation, and/or at least once every 5 minutes of operation.

In some embodiments, the control system is configured to alter at least one property of the whole broth within the vessel resulting in an improvement in at least one of bioproduct yield, bioproduct quality, bioproduct purity, bioproduct production rate, reduced cost, reduced energy consumption, and reduced waste generation, relative to a system that is controlled manually. In some embodiments, the aseptic sampling system is operably connected to the control system.

In some embodiments, a system for making a bioproduct includes a vessel capable of providing an environment suitable for containing whole broth that can produce the bioproduct. The whole broth contains media and at least one undissolved species. The system also contains at least one analytical instrument operably connected to the vessel, the at least one analytical instrument being configured to measure at least one cell-level property of the whole broth in the vessel and generating at least one signal in response thereto. A control system is provided that in response to the at least one signal generates at least one output signal capable of controlling a device that is configured to alter at least one property of the whole broth within the vessel.

The foregoing and other objects, features, and advantages of the invention will become more apparent from the following detailed description, which proceeds with reference to the accompanying figures.

DETAILED DESCRIPTION

Figure 1:
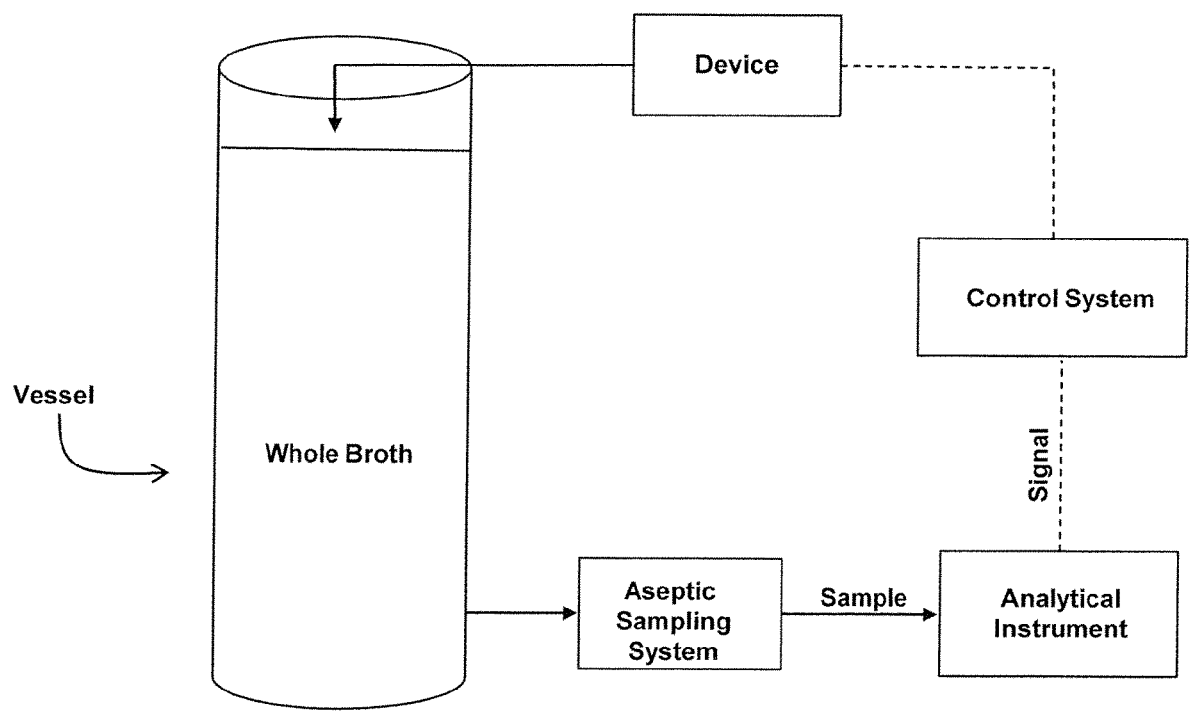
FIG. 1 illustrations a schematic of one embodiment of the invention.

Various embodiments of systems and their methods of use are disclosed herein. The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

The terms "upstream" and "downstream" are not absolute terms; instead, those terms refer to the direction of flow of fluids within a channel or pathway. Thus, with regard to a structure through which a fluid flows, a first area is "upstream" of a second area if the fluid flows from the first area to the second area. Likewise, the second area can be considered "downstream" of the first area.

Unless otherwise indicated, all numbers expressing quantities of ingredients, properties such as molecular weight, percentages, measurements, distances, ratios, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

As described herein, various systems and methods are provided for obtaining samples from or measuring properties of a bioreactor (or other systems that support biologically and/or chemically active environments) and altering the inputs to and/or environment of the bioreactor to adjust the growth or productivity of the media in the bioreactor based on information obtained. In one embodiment, the information obtained includes media level information. In another embodiment, the information obtained includes cellular level information. In yet another embodiment, the information obtained includes both media level information and cellular level information.

As used herein, bioproducts (also known as bio-based products) are materials, chemicals, and energy derived from renewable biological resources. Examples of bioproducts include foods, beverages, biofuels, bioenergy, bio-based ethanol, biodiesel, bio-based adhesives, biochemicals, biotherapeutics, biodegradable plastics, and mixtures thereof. Specific examples of bioproducts include antibiotics, amino acids, enzymes, monomers, proteins, food cultures, biopolymers, ethanol, isopropanol, isobutanol, flavorings, perfume chemicals, and the like.

Bioreactors

Bioproducts are made in bioreactors, which are systems that support a biologically active environment. Examples of bioreactors include fermenters (anaerobic or aerobic), stirred-tank reactors, adherent bioreactors, wave-type bioreactors, and disposable bioreactors. A bioreactor can include, for example, a large fermentation chamber for growing organisms that can be used to produce bioproducts.

Bioreactors generally contain whole broth. As used herein, the term "whole broth" means the contents of the bioreactor (or a portion thereof), including "media" and "undissolved" species. As used herein, the term "media" means the liquid phase, including all dissolved substances, such as nutrients, dissolved organics, ionic species, etc. As used herein, the term "undissolved" species means the live cells, dead cells, cell fragments, solid substrates having cells adhered thereto, or other particles present in the whole broth. In one embodiment, the live cells are selected from bacteria, yeast, mammalian cells, and *e-coli* cells.

In one example, bio-therapeutic proteins can be produced from genetically modified mammalian cells within a bioreactor. Such production can be from cell lines of established cell cultures, such as, for example, CHO, NS0, or PER.C6. These cells express the protein of interest and subsequently secrete the protein into the media. In many instances, mammalian cells are grown in a fed-batch process; however, it should be understood that the methods and systems disclosed herein can be applicable in perfusion type cell culture systems.

In some instances, bioreactors can be configured to adjust or control inputs to the bioreactor, including, for example, one or more of the following variables of pH, dissolved oxygen (DO), reactant/nutrient concentrations, temperature, and agitation. Such bioreactors can include stirred-tank type reactors, as well as adherent bioreactors, wave-type bioreactors, and disposable bioreactors.

Bioreactors are typically equipped with a means for mixing or agitating the whole broth in the bioreactor, including using mechanical mixing, circulation pumps, shifting baffle plates, mechanical vibration schemes, ultrasonic agitation, acoustic agitators, gas bubble agitators, vortex generators, cavitation pumping, and combinations thereof. Bioreactors also typically are equipped with heat exchangers for maintaining or controlling the temperature in the bioreactor.

Analysis of the Whole Broth

The whole broth can be analyzed to provide insight into the contents of the bioreactor. The analysis of the whole broth can include a determination of one or more properties of the media within the bioreactor, a determination of one or more properties of undissolved species (e.g., cells) contained in the whole broth, or both a determination of one or more properties of the media within the bioreactor and a determination of one or more properties of undissolved species contained within the bioreactor.

Media Level Process Analytical Technologies

A bioreactor can be analyzed for media level information. Such media level process analytical technologies (PAT) can be used to measure certain analytes or properties of the media including, for example, pH, dissolved oxygen (DO), osmolality, glucose or other carbon sources, ammonia/ammonium, lactate/lactic acid, pCO2, electrolytes (such as K+, Ca++, and/or Na+), amino acids, and NAD/NADH concentrations. Bioproduct purity, impurities levels, and other parameters may also be measured. Analytical instruments include pH probes, dissolved oxygen meters, ion-selective electrodes, osmometry, high-performance liquid chromatography, ultra performance liquid chromatography, gas chromatography, ion chromatography, conductivity, Raman spectroscopy, near infrared (NIR) spectroscopy, dielectric spectroscopy, fluorometry, ultraviolet/visible spectroscopy, capacitance probes, luminescence, and redox probes.

Cell Level Process Analytical Technologies

A bioreactor can also be analyzed for cellular properties (part of the undissolved species in the whole broth) which may be indicative of, for example, cell behaviors, phenotypes, metabolic states, health, and/or cell cycle. Such cellular level PATs can include, for example, dielectric spectroscopy (to determine electrical cell properties), flow cytometry (either incorporating staining of organelles or not), Raman/NIR spectroscopy (which can provide information about cell health in certain cases), automated hemacytometer, electro-rotation, electrophoresis, and/or dielectrophoresis.

Process Controls Based on Sample Analysis

In the embodiments described herein, a data-rich, cell-level PAT, such as dielectric spectroscopy or the other measurement tools described herein, can be used to measure or characterize an aspect of cell behavior within a sample. In addition, in some embodiments, a data-rich, media-level PAT device can also be used in conjunction with the cell-level PAT. For example, a chemistry analyzer can be provided and at least a portion of the sample can be directed to the chemistry analyzer to obtain additional information about the media of the sample. The result is a system where the interaction of process conditions and cells can be obtained, thereby enabling process control (as described in more detail below) based at least in part on cell behavior, rather than treating the cells as a black-box and controlling only whole broth parameters. In some embodiments, the interaction of process conditions and cells can be observable on-line and in real time, thereby enabling on-line process control.

FIG. 1 illustrates a schematic of one embodiment of the invention. Here, a vessel is charged with whole broth. An aseptic sampling system removes a sample of whole broth from the vessel and directs it to at least one analytical instrument. The analytical instrument generates a signal in response to the composition of the sample, the signal sending a signal to a control system. A control system can be provided to control, monitor, and/or communicate with any of the devices/instruments described herein. For example, the control system can be configured to perform various tasks, including controlling operation of the sampling system, receiving information from analytical instruments, and/or controlling the operation of the devices or instruments provided herein to alter the environment of the bioreactor, Thus, for example, the control system can be configured to receive information from one or more analytical instruments and, in response to that received information, send one or more control signals to one or more devices instructing such devices to alter at least one property of the whole broth within the vessel.

In some embodiments, the control system can be configured to communicate with the aseptic sampling system and/or to control operation of the aseptic sampling system. For example, the control system can send one or more signals to the sampling system to instruct the sampling system to obtain a sample of whole broth and/or to determine when a sample of whole broth is removed from the vessel.

In addition to controlling, monitoring, and/or analyzing various applications relating to the bioreactor, the control system can be configured to display information to a user, including, for example, information about drawing of a sample, information about the analysis of the sample (e.g., as provided by the analytical instrument(s)), and/or information about the operation of various devices/instruments that are being monitored and/or controlled by the control system.

Figure 2:
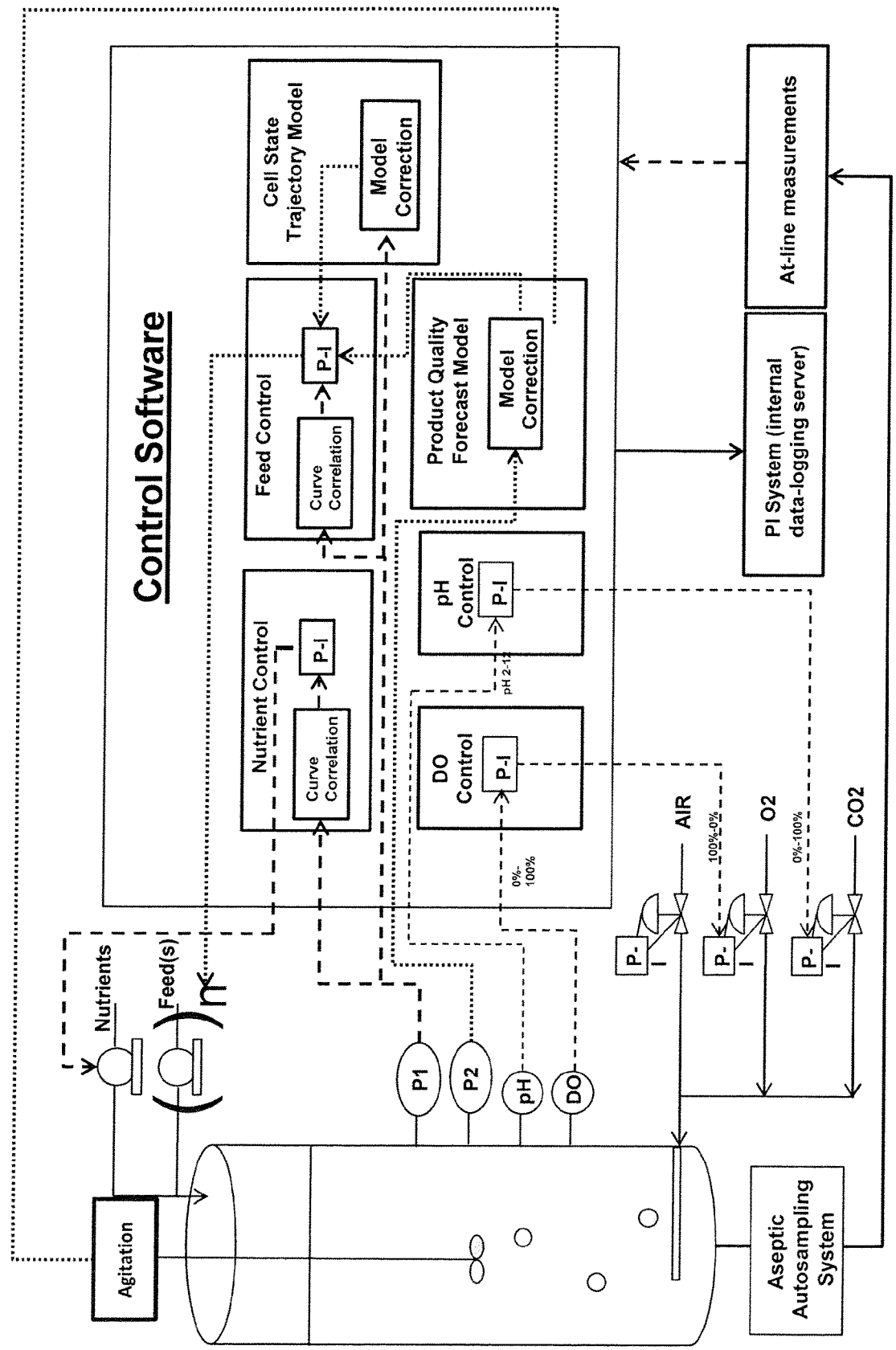
FIG. 2 illustrates a schematic control system for controlling the operation of a bioreactor or other such system by analyzing a sample to provide media and/or cellular level information about the sample.
Figure 3:
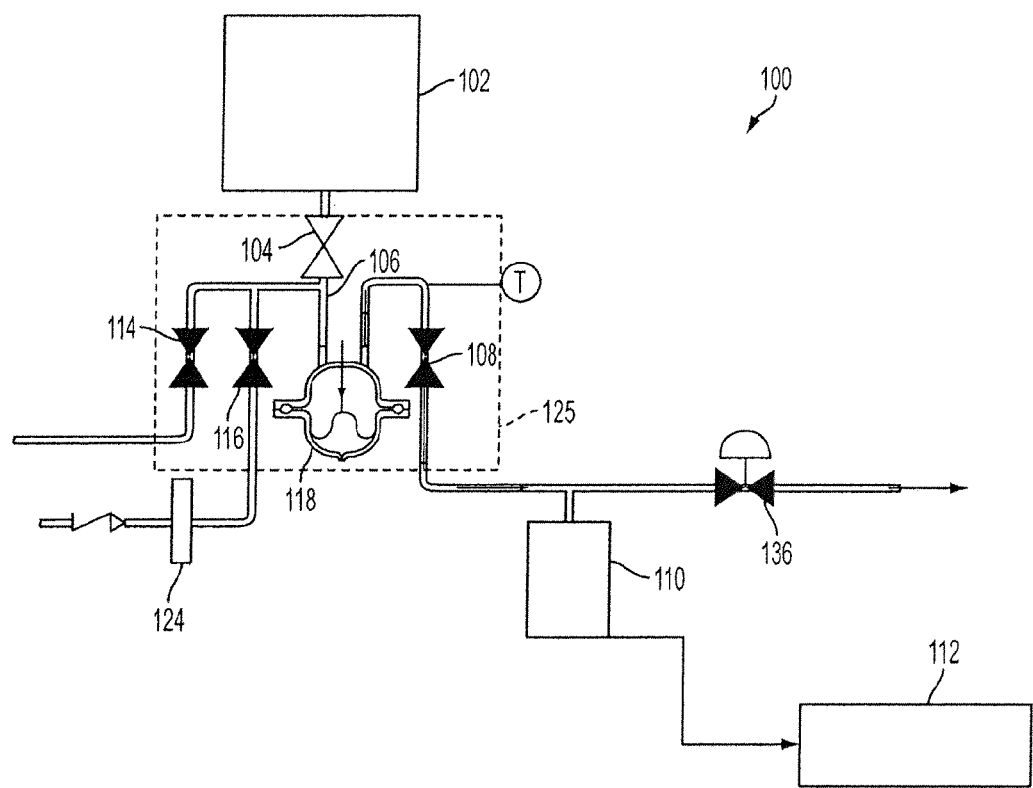
FIG. 3 illustrates a schematic view of an aseptic autosampling system for obtaining samples from enclosed containers.

FIG. 2 illustrates an exemplary control schematic for manipulating variables in a bioreactor process based on the performance of one or more analytical instruments to measure a media and/or cellular level attributes of a sample. As shown in FIG. 3, one or more samples can be drawn from a vessel, such as a bioreactor by a sampling device, such as an automated sampling device. The sample (or samples) can be analyzed by one or more process analytical technologies (PATs) to identify various attributes of the media, the cells in the whole broth, and/or both. The PATs can be performed by one or more devices that are operatively coupled to the sampling device to perform at-line measurements of the sample(s).

Alternatively, or in addition to the at-line measurements, the PATs can directly measure the attributes of the media or cells directly in the bioreactor using in situ devices (that is, not through a sampling device). The results of these PATs can be provided to a control system (indicated in FIG. 2 as Control Software) and the control system can provide adjustments to the inputs to the bioreactor and/or to the environment within the bioreactor. For example, as shown in FIG. 2, various systems can be provided for controlling variables such as nutrient concentration (e.g., by increasing or decreasing the flow of nutrients to the bioreactor), DO, pH, or agitation rates. In addition, as shown in FIG. 2, various models can be applied to the control system to adjust the inputs and/or environment based on an understanding of cell state trajectory or product quality forecasts that were developed by prior modeling efforts.

A sample can be drawn from the bioreactor and one or more media and cellular level PATs performed on at least a portion of the sample that is drawn from the bioreactor. In another embodiment, the cellular and media level PATs can be measured using an in situ device connected to the vessel. In one embodiment, the sample can be drawn by an aseptic autosampling system such as the system described herein with respect to FIG. 3. However, it should be understood that other sampling devices can be used to draw a sample from the system, including, for example, any manual and/or automatic system that is capable of drawing sample from the system.

As shown in FIG. 2, a centralized control platform can be provided to receive the results of the various PATs and to provide real-time process adjustments to the process to alter the environment within the bioreactor in accordance with information obtained from the PATs performed on the sample.

In one embodiment, the cellular behavior and how it manifests in the process variables from the PAT can be characterized in off-line studies. In that manner, the information obtained from the off-line studies can be used to provide understandings of how the cell states reflected in the PATs can be used to identify desired changes in the process to provide improved production and/or yield. For example, the identification of key biomarkers or causes of impurity formation can be developed in off-line studies and that information can be used to provide future real-time adjustments to the process. Such off-line studies can provide relevant modeling information about the current sample based on previous samples, thereby allowing corrective actions to be made to the bioreactor in real time.

Accordingly, the new observability provided by the PATs described herein can be used to create a control model, whereby manipulation of individual (or groups) of process variables will affect the output product in a predictable way. This can be accomplished via multi-variate statistical methods like Multi-Variate Analysis (MVA), or in some examples, by uni-variate type correlations. After this information is obtained, the control model can run in real-time in a process control environment in order to accomplish the feed-back control as shown in FIG. 2.

The variables manipulated by the centralized control platform can be any process variable or combination of process variables that is found during development to affect cell behavior and therefore the product. For example, variables that can be manipulated by the centralized control platform in response to PATs can include pH, DO, glucose or carbon source concentration, osmolality, feed flow rate, feed composition, temperature, and/or agitation/shear.

In one embodiment, the control system in response to the signal generates at least one output signal capable of controlling at least one device that is configured to alter at least one property of the whole broth within the vessel. Devices suitable for this include mixing/agitation systems, temperature-control systems, gas pumps, nutrient pumps, product removal systems, impurity removal systems, pH adjustment systems, and mixtures thereof.

Sampling Systems and Methods

Obtaining samples from bioreactors that support biologically and/or chemically active environments can provide helpful insight about the media contained with a within the bioreactor. Samples can be obtained from bioreactors in various ways, including some that require manual efforts to draw the sample from the bioreactor and those that are configured to automatically obtain the sample. For example, manual samples can be obtained by directly inserting a sampling device into the bioreactor or otherwise drawing a sample directly from within the bioreactor.

The following description illustrates an exemplary automated sampling system that can be used with the systems and methods of producing biotherapeutics disclosed herein. As described in more detail below, the automated sampling system disclosed herein can reduce the risk of contamination between the drawing of different samples from the bioreactor.

FIG. 3 illustrates a sampling system 100 for obtaining a sample from a bioreactor 102 or other similar containers or systems that support biologically and/or chemically active environments. Sampling system 100 includes a sample collection valve 104 that can open to allow a sample to enter a fluid flow path 106. The sample can be delivered along the flow path 106 to an outlet valve 108. Outlet valve 108 can open or close to allow or restrict, respectively, the flow of samples through outlet valve 108. After the sample exits outlet valve 108, the sample can be directed into an isolated chamber or container 110 for analysis, processing, and/or delivery to another system for analysis and/or processing. For example, the sample can be directed from chamber 110 to an automated analyzer 112, such as a bioprofile analyzer available from Nova Biomedical of Waltham, Massachusetts.

The samples that are dispensed from outlet 108 for analysis or processing are desirably representative of the materials in bioreactor 102 at the time the sample was taken. To reduce the risk of contamination, dilution, or alteration of the composition of the samples taken from sample collection valve 104 and delivered through flow path 106, a sanitizing fluid can be delivered through a portion of flow path 106 that comes into contact with the samples.

To introduce the sanitizing fluid into flow path 106, a sanitizing fluid inlet valve 114 is provided upstream of sample collection valve 104. Sanitizing fluid inlet valve 114 is operable between a closed position that restricts fluid flow through sanitizing fluid inlet valve 114 and an open position that allows fluid flow through sanitizing fluid inlet valve 114. In one embodiment, the sanitizing fluid comprises steam.

A gas inlet valve 116 can also be provided upstream of sample collection valve 104 to deliver a gas through flow path 106. The gas can eliminate and/or reduce the amount of sanitizing fluid remaining within flow path 106 after flow path 106 is exposed to the sanitizing fluid. Gas inlet valve 116 is operable between a closed position that restricts the flow of gas through gas inlet valve 116 and an open position that allows the flow of gas through gas inlet valve 116. In one embodiment, the gas comprises compressed air.

To draw a sample from bioreactor 102, a variable volume reservoir 118 can be provided downstream of sample collection valve 104. Variable volume reservoir 118 can be moveable between a first position and a second position to draw a sample through sample collection valve 104 and into flow path 106. The sample can be drawn into at least a portion of variable volume reservoir 118 along a first portion of flow path 106 and discharged from variable volume reservoir 118 along a second portion of flow path 106. Variable volume reservoir 118 can comprise a diaphragm pump (as shown in FIG. 3), a syringe pump, or other similar device capable of drawing a sample from bioreactor 102.

As shown by dotted lines in FIG. 3, at least a portion of sampling system 100 can comprise a unitary structure 125. Thus, for example, unitary structure 125 can comprise sample collection valve 104, sanitizing fluid inlet valve 114, gas inlet valve 116, outlet valve 108, and at least a portion of the fluid flow path. Preferably, the entire flow path between the sanitizing fluid inlet valve 114 and the outlet valve 108 is internal to the unitary structure 125.

FIGS. 4A-4D are schematic representations of the operation of sampling system 100. As described in more detail below, sampling system 100 can be inserted into bioreactor 102 and can operate to sanitize or sterilize a flow path from the point of insertion with bioreactor 102 through the closed pathway of flow path 106. By being able to sanitize or sterilize the entire path downstream of the insertion point of sampling system 100 into bioreactor 102, the possibility of contaminating bioreactor 102 and/or the samples captured from bioreactor 102 is reduced.

Figure 4A:
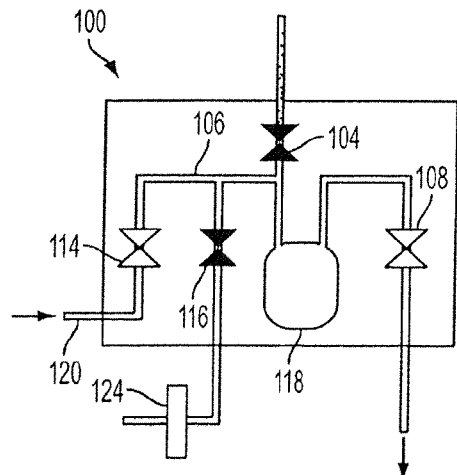
FIGS. 4A-4D illustrate schematic views of a system for obtaining samples from enclosed containers.

FIG. 4A illustrates a sanitizing procedure in which a sanitizing fluid 120 (e.g., steam) is directed into flow path 106 through an open sanitizing fluid inlet valve 114. As shown in FIG. 4A, sanitizing fluid 120 is directed along flow path 106, including along the portions of flow path 106 that are in contact with samples that are drawn from bioreactor 102 and dispensed from flow path 106. For example, sanitizing fluid 120 is directed along flow path 106 past sample collection valve 104, through variable volume reservoir 118, and out outlet valve 108. As sanitizing fluid 120 comes into contact with the internal surfaces that define flow path 106, those surfaces are sanitized or sterilized.

Figure 4B:
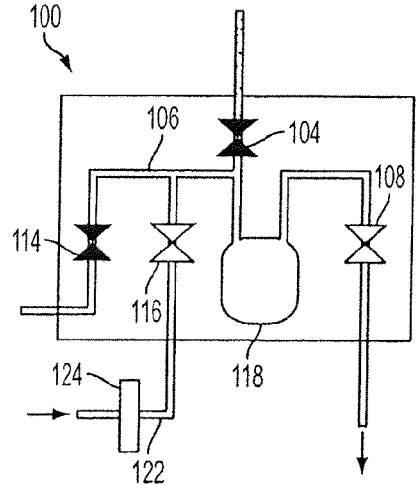

Referring now to FIG. 4B, sanitizing fluid inlet valve 114 is closed and gas inlet valve 116 is opened to allow a gas 122 (e.g., air) to enter flow path 106. As shown in FIG. 4B, gas 122 can also be directed along flow path 106, including along the portions of flow path 106 that sanitizing fluid 120 contacts. In this manner, any remaining sanitizing fluid 120 can be purged from flow path 106. If desired, a filter 124 (e.g., a sterile air filter) can be provided upstream of gas inlet valve 116 to ensure that the gas 122 that enters flow path 106 is substantially free of impurities and/or contaminants.

Figure 4C:
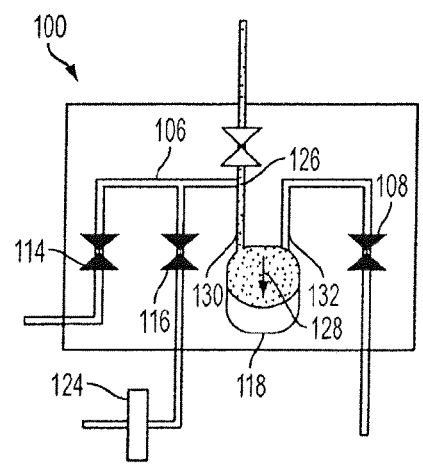
Figure 4D:
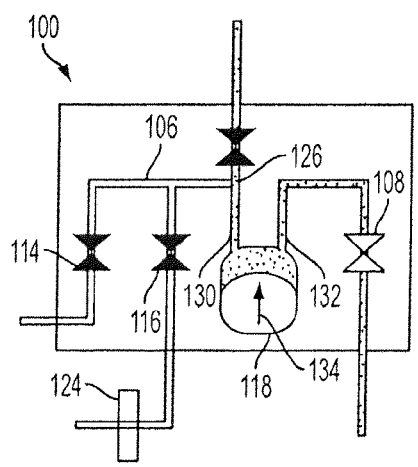

FIG. 4C illustrates the operation of variable volume reservoir 118 to draw a sample 126 from bioreactor 102 through open sample collection valve 104. As shown in FIG. 4C, variable volume reservoir 118 comprises a diaphragm pump that moves from a first volume to a second, larger volume as illustrated by arrow 128. The enlargement of the volume of variable volume reservoir 118 draws a sample through open sample collection valve 104 and into flow path 106. Variable volume reservoir 118 has an inlet 130 and an outlet 132. After sample 126 is drawn into variable volume reservoir 118, the diaphragm pump moves from the second, larger volume back to a smaller volume as illustrated by arrow 134 in FIG. 4D. The reduction of the volume of variable volume reservoir 118 discharges sample 126 through outlet 132 of variable volume reservoir 118. Sample 126 is then discharged through outlet valve 108 to be captured for analysis and/or further processing.

Referring again to FIG. 3, as sample 126 is discharged through outlet valve 108, it can be delivered to chamber 110. To facilitate delivery of sample 126 to chamber 110, a control valve 136 can be provided downstream of outlet valve 108. Control valve 136 can be configured to provide a back pressure to cause sample 126 to be directed into chamber 110 and to provide a desired back pressure along flow path 106 to facilitate the sanitizing process (e.g., FIG. 4A) and the purging process (e.g., FIG. 4B). Control valve 136 can be configured to open to allow the discharge of waste. The discharged waste can include, for example, sanitizing fluid and purging gas that has traveled along the flow path 106 to sanitize and purge excess sample materials from flow path 106.

Figure 5A:
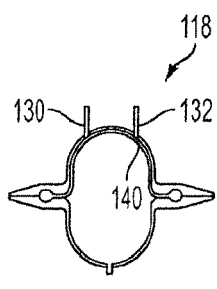
FIGS. 5A-5F illustrate a variable volume reservoir for drawing and delivery samples from enclosed containers.
Figure 5B:
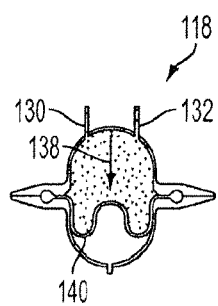
Figure 5C:
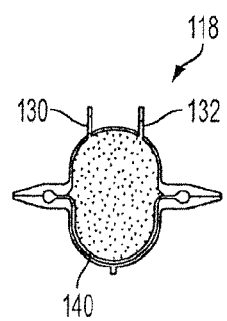
Figure 5D:
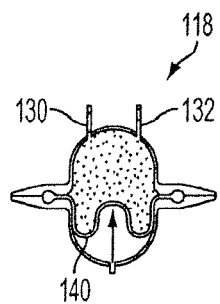
Figure 5E:
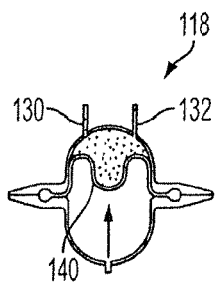
Figure 5F:
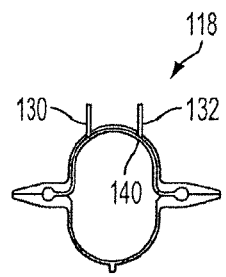

FIGS. 5A-5F illustrate an exemplary operation of a variable volume reservoir 118. FIG. 5A illustrates variable volume reservoir 118 in a first configuration with a very small volume (e.g. approximately zero volume). FIG. 5B illustrates a sample being drawn into variable volume reservoir 118 through inlet 130, thereby moving a diaphragm 140 of variable volume reservoir 118 in the direction of arrow 138. Diaphragm 140 can continue to move in the direction of arrow 138 and expand the volume of variable volume reservoir 118 until variable volume reservoir 118 reaches a second configuration with a larger volume as shown in FIG. 5C. As shown in FIGS. 5D, 5E, and 5F diaphragm 140 can then move from the second configuration to the first configuration, causing the sample contained within variable volume reservoir 118 to be discharged through outlet 132.

FIGS. 6A-6D illustrate another embodiment of a sampling system 200. Sampling system 200 is generally similar to sampling system 100 and like elements are identified by similar reference numbers. The main differences between sampling system 100 and 200 are illustrated in the various figures and described in the related descriptions of those systems as included herein.

Figure 6A:
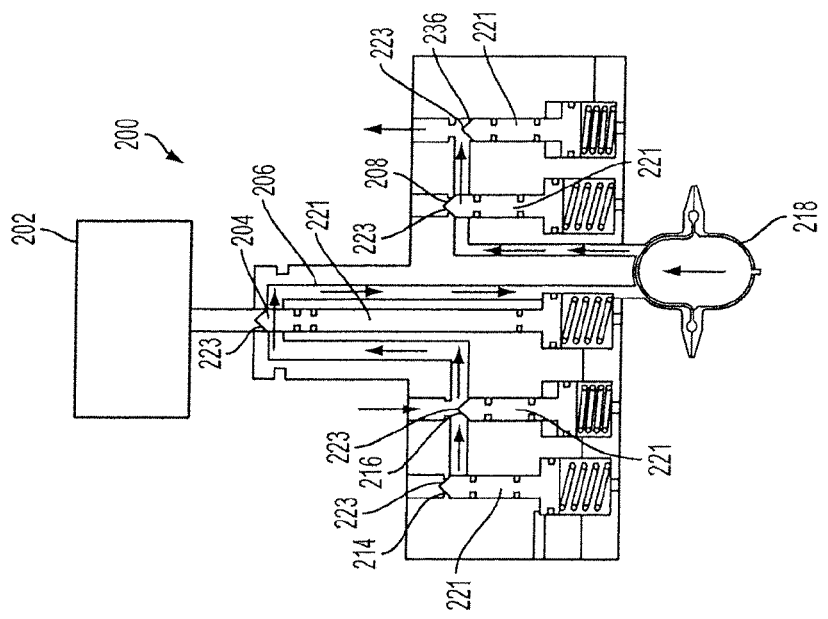
FIGS. 6A-6D illustrate schematic views of another system for obtaining samples from enclosed containers.

Sampling system 200 can include a sample collection valve 204, an outlet valve 208, a sanitizing fluid inlet valve 214, and a gas inlet valve 216. One or more of these valves can be configured to have a valve stem 221 and a sealing member 223. Although FIG. 6A illustrates each of these valves as having a valve stem 221 and a sealing member 223, it should be understood that the type of valve can vary. The valve stems can be actuated by springs or air, and preferably by a combination of spring- and air-actuation.

FIG. 6A illustrates a sanitizing or sterilizing process. During the process shown in FIG. 6A, sample collection valve 204, outlet valve 208, and gas inlet valve 216 are closed with sealing members 223 moved into engagement with the respective openings associated with those valves into flow path 206. Thus, for example, the sealing member 223 of sample collection valve 204 is engaged with an opening between flow path 206 and bioreactor 202 to restrict the passage of material in bioreactor 202 from entering flow path 206. At least a portion of the valve stem 221 associated with the sample collection valve 204 extends into flow path 206, but does not entirely block flow path 206. In this manner, sanitizing fluid can pass across a portion of the sample collection valve 204 (and other valves in a similar manner) to sterilize and sanitize the portions of the valve that is in flow path 206. Thus, as shown in FIG. 6A, sanitizing fluid is directed through flow path 206 across the closed gas inlet valve 216, across the closed sample collection valve 204, through the variable volume reservoir 218, across the closed outlet valve 208, and out an open control valve 236. Contaminants and other materials caught up in the sanitizing fluid can also exit control valve 236.

Figure 6B:
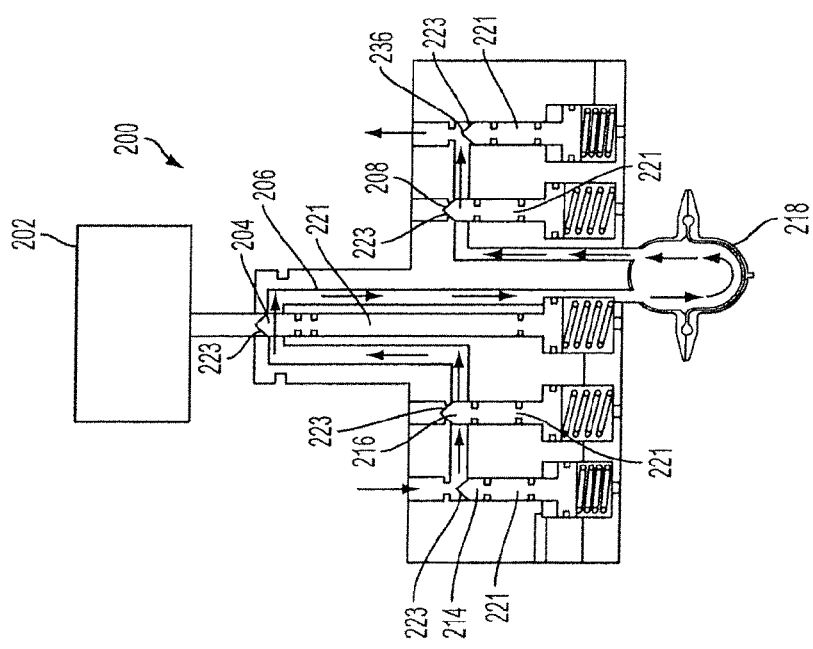

Referring to FIG. 6B, the sanitizing fluid inlet valve 214 can be closed and gas inlet valve 216 can be opened to deliver a purging gas (e.g., air) through flow path 206 to remove and/or reduce the presence of sanitizing fluid within flow path 206. The gas is directed through flow path 206 across the closed gas inlet valve 216, across the closed sample collection valve 204, through the variable volume reservoir 218, across the closed outlet valve 208, and out the open control valve 236.

Figure 6C:
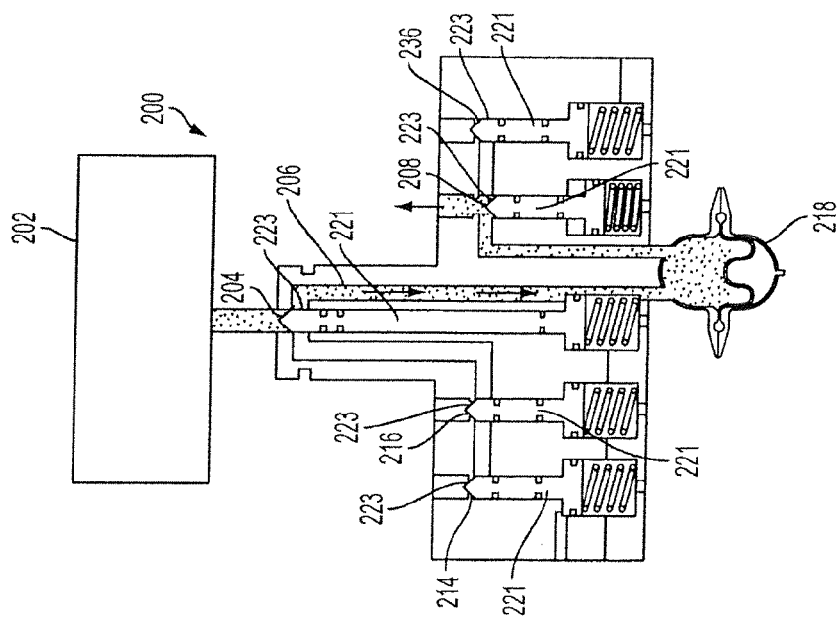
Figure 6D:
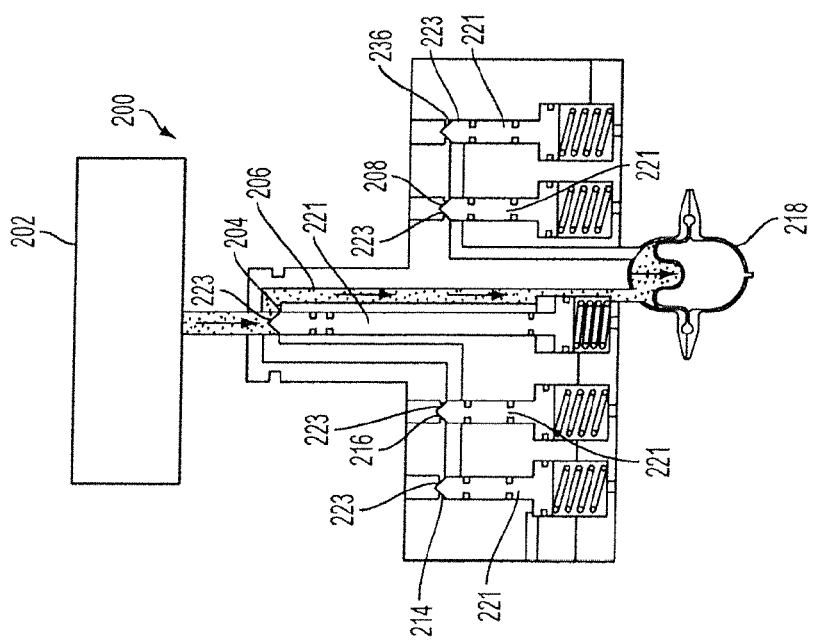

Once the gas purges the remaining sanitizing fluid from flow path 206, both the sanitizing fluid inlet valve 214 and the gas inlet valve 216 can close to allow a sample to be drawn into flow path 206. As shown in FIG. 6C, variable volume reservoir 218 draws a sample through the open sample collection valve 204 and into the volume of variable volume reservoir 218. Variable volume reservoir 218 then directs the drawn sample further downstream along flow path 206 towards outlet valve 208 as shown in FIG. 6D. Outlet valve 208 can open to allow the sample to be discharged from flow path 206.

Figure 7C:
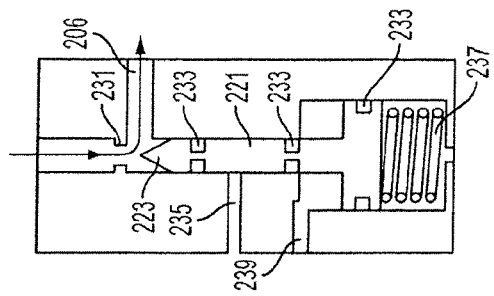
FIGS. 7A-7C illustrate enlarged views of exemplary valves that can be used with a sampling system.
Figure 7B:
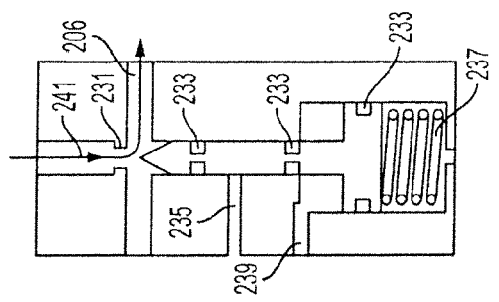
Figure 7A:
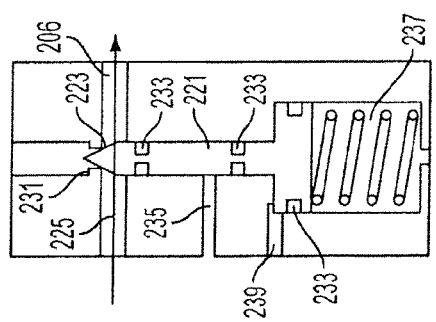

FIGS. 7A-7C illustrate enlarged views of exemplary valves that can be used with the systems disclosed in FIGS. 6A-6C. For example, FIGS. 7A and 7B illustrate a three-way bypass flow valve that can move between an open configuration (FIG. 7A) and a closed configuration (FIG. 7B). In FIG. 7A, valve stem 221 is shown extending into flow path 206 with sealing member 223 closing a port 231 (e.g., a gas inlet port, a sample collection inlet port, a sample collection outlet port) into flow path 206. In the closed configuration, fluid can flow past valve stem 221 as shown by arrow 225. One or more sealing rings 233 (e.g., O-rings) can at least partially surround valve stem 221 to restrict the flow of fluid out of flow path 206 in the area of valve stem 221. In addition, a weep hole 235 can be provided to further remove any moisture of other fluids that may move past sealing rings 233.

A spring 237 can be provided to bias valve stem 221 towards the closed configuration (FIG. 7A) and to ensure that sealing member 223 seats itself properly with port 231. An air inlet 239 can be provided adjacent valve stem 221 to move valve stem 221 from the closed configuration (FIG. 7A) to the open configuration (FIG. 7B). Compressed air or other fluids can be directed through air inlet 239, causing valve stem 221 to move downward as shown in FIG. 7B. As valve stem 221 moves downward, sealing member 223 moves out of engagement with port 231, allowing fluid to pass through port 231 and enter flow path 206 as shown by arrow 241.

FIG. 7C illustrates a two-way valve that is moveable between a closed configuration (not shown) and an open configuration (FIG. 7C). As shown in FIG. 7C, a valve stem 221 with a sealing member 223 can move into an open configuration in the same manner as that shown in FIG. 7B. Such a valve can be used, for example, with a port 231 that is configured to be opened and closed to allow fluid to flow into the pathway, such as a sanitizing fluid inlet port or a waste outlet port.

Figure 8:
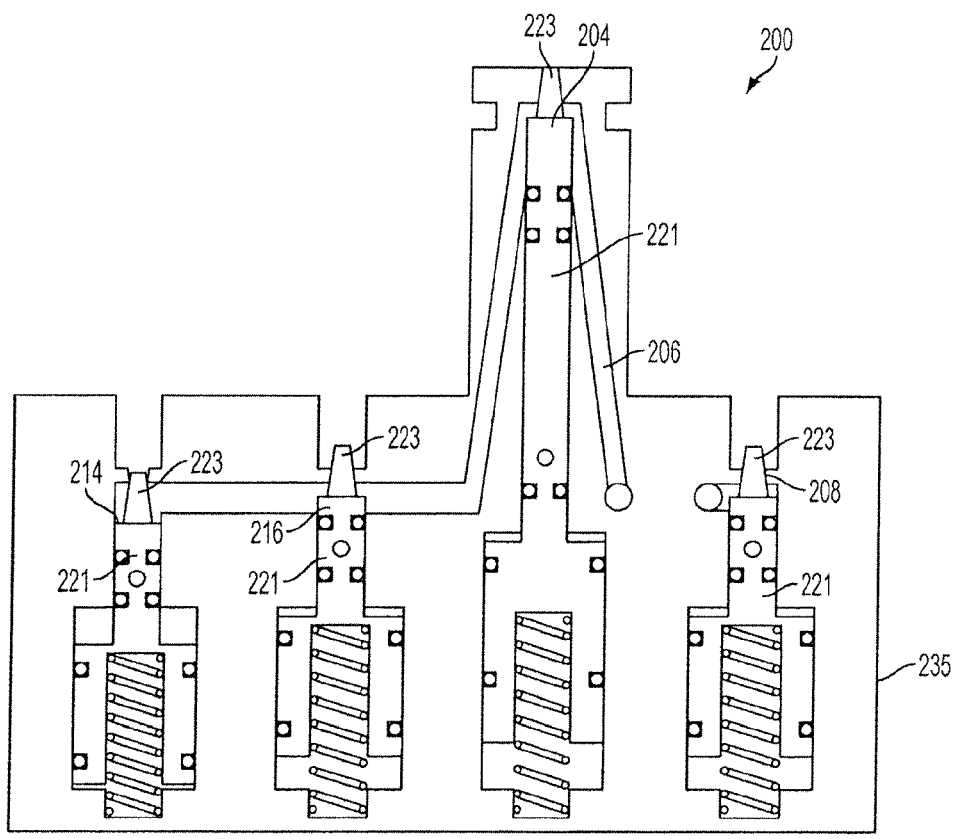
FIG. 8 illustrates a cross-sectional view of a system for obtaining samples from enclosed containers.

FIG. 8 illustrates a cross-sectional view of a portion of another exemplary sampling system 200, shown with an angled fluid path 206 between the sanitizing fluid inlet valve 214 and the outlet valve 208. Sample collection valve 204 extends from a main body 235 of sampling system 200 to facilitate coupling of sample collection valve 204 with bioreactor 202 (not shown in FIG. 8).

Figure 9:
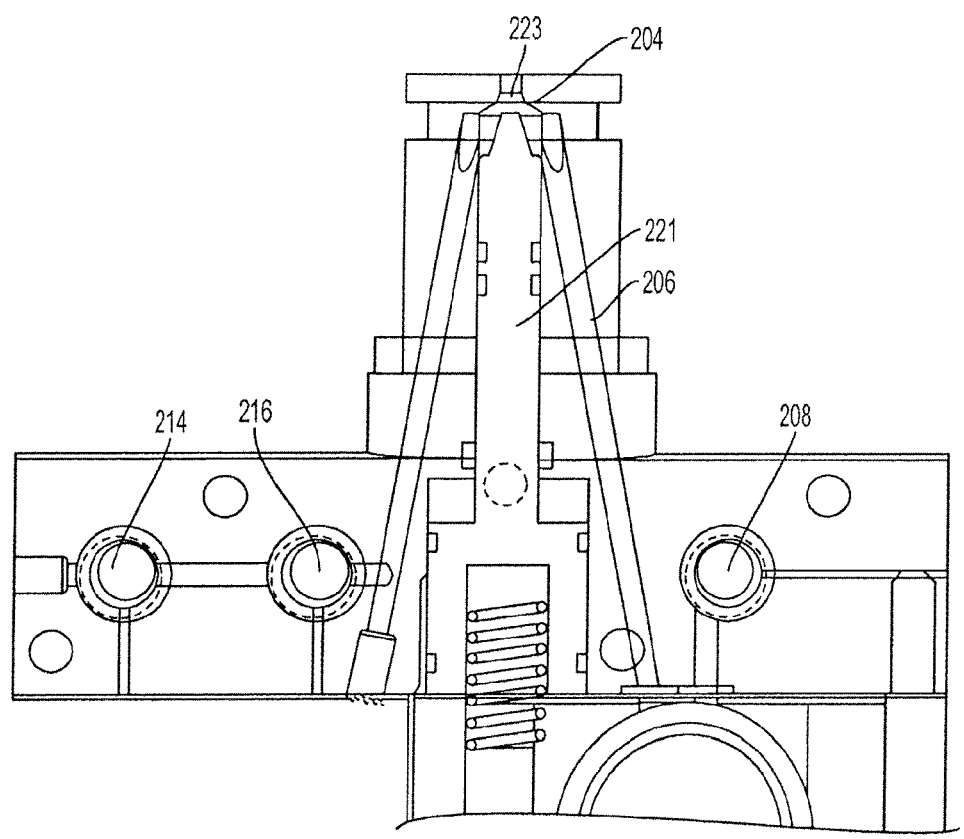
FIG. 9 illustrates a partial cross-sectional view of a system for obtaining samples from enclosed containers.
Figure 10:
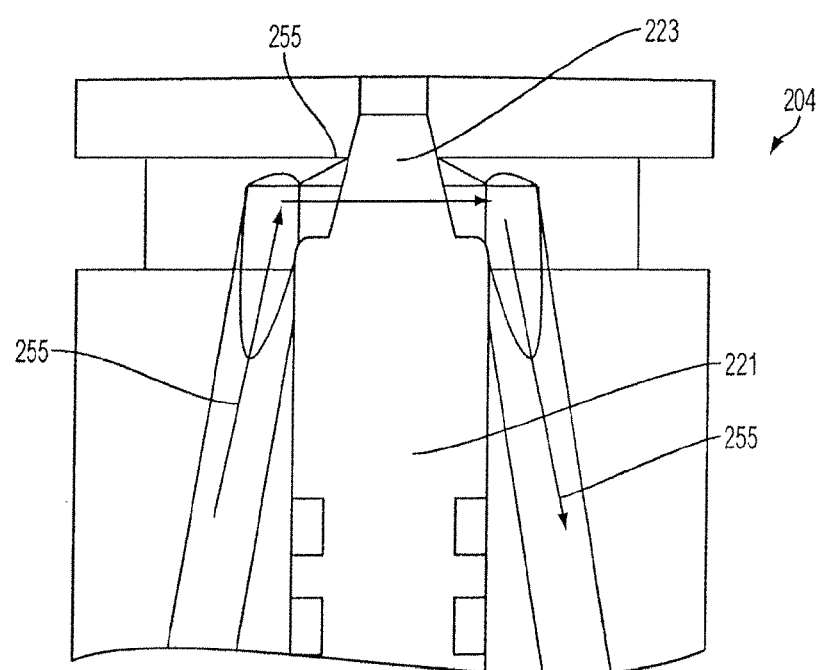
FIG. 10 is an enlarged view of a portion of the system shown in FIG. 5.

FIGS. 9 and 10 illustrate views of portions of another exemplary sampling system 200, also having an angled fluid path 206 between the sanitizing fluid inlet valve 214 and the outlet valve 208. As shown in the enlarged partial cross-sectional view of FIG. 9, when sample collection valve 204 is in a closed position (e.g., with a sealing member 223 extending into an opening between the bioreactor and flow path 206), sanitizing fluid can flow around the end of valve stem 221. Thus, for example, as shown by arrows 255, sanitizing fluid can pass around a portion of sample collection valve 204, thereby improving sanitization or sterilization of the area adjacent the opening extending into the bioreactor.

Moreover, by forming sample collection valve with a sealing member 223 that tapers from valve stem 221, the area of contact between sealing member 223 and the opening can be reduced. To provide improved sealing characteristics, in some embodiments, the tip of the valve stem can extend at an angle of greater than 50 degrees from the body of the valve stem and, more preferably at an angle of greater than 70 degrees and, even more preferably at an angle of about 80 degrees.

Figure 11:
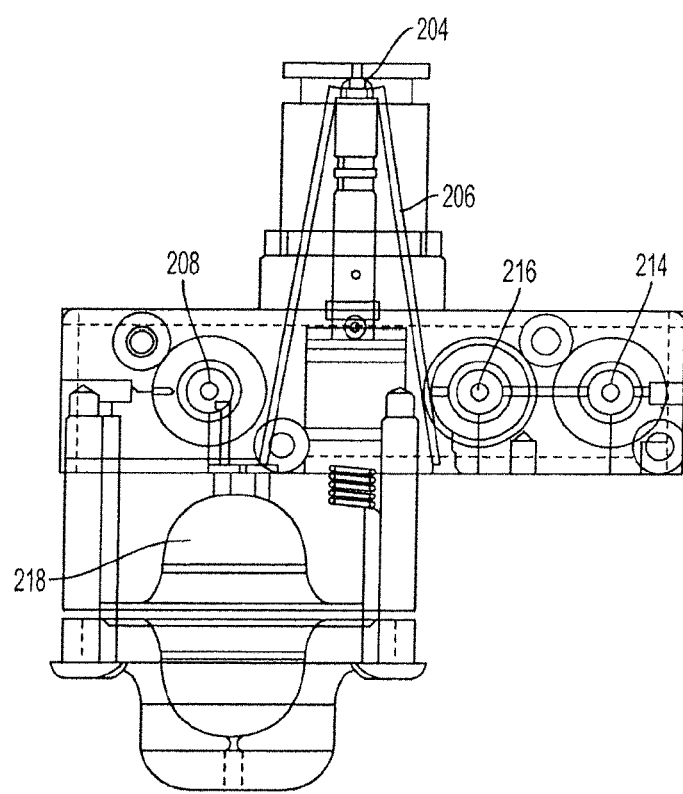
FIG. 11 illustrates another embodiment of a system for obtaining samples from enclosed containers.

FIG. 11 illustrates another embodiment of sampling system 200, with a variable volume reservoir 218 integrally formed with the sampling system structure. Variable volume 218 comprises a diaphragm pump connected flow path 206 to draw samples from the bioreactor (not shown) to which sampling system 200 is coupled.

As described above with respect to FIG. 3, a control valve 136 can be provided downstream of outlet valve 108. Control valve 136 can be configured to provide a desired back pressure along flow path 106 to facilitate the sanitizing process (e.g., FIG. 4A), the purging process (e.g., FIG. 4B), and/or the sample collection process (e.g., FIG. 4D). For example, during the sanitizing process, it is desirable to keep the sanitizing fluid at a desired temperature for a desired length of time (e.g., if steam is the sanitizing fluid it can be desirable to maintain the steam at about 121° C.). By providing back pressure via the control valve, the temperature within the flow path during the sanitizing process can be more easily maintained.

Figure 12:
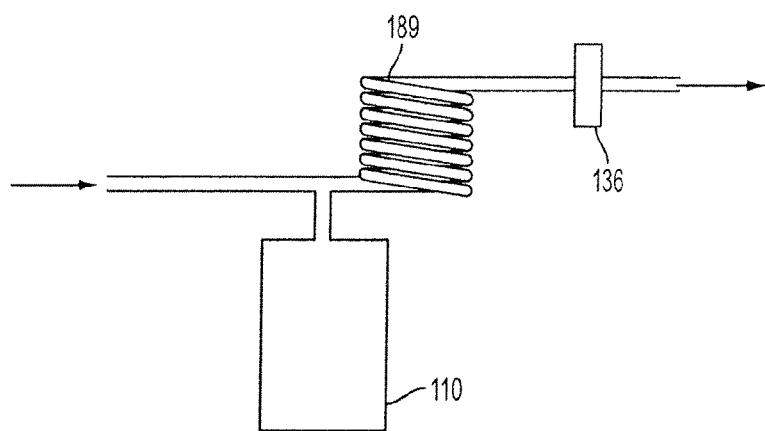
FIG. 12 illustrates a partial view of a portion of a system for obtaining samples from enclosed containers.
Figure 14:
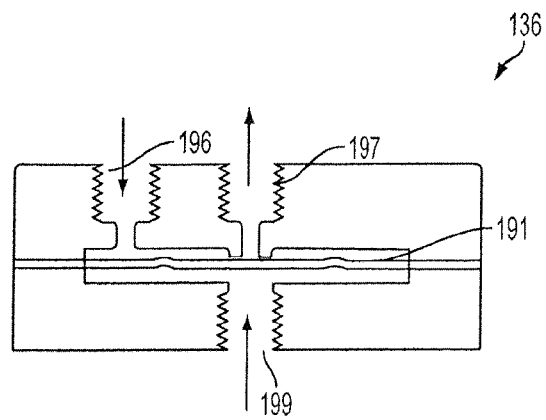
FIG. 14 illustrates another view of the control valve of FIG. 10.
Figure 13:
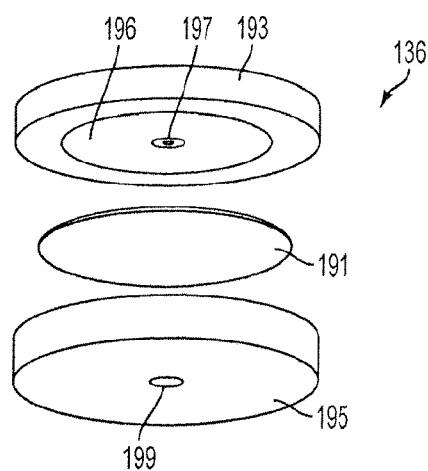
FIG. 13 illustrates a control valve for use with a system for obtaining samples from enclosed containers.
Figure 15A:
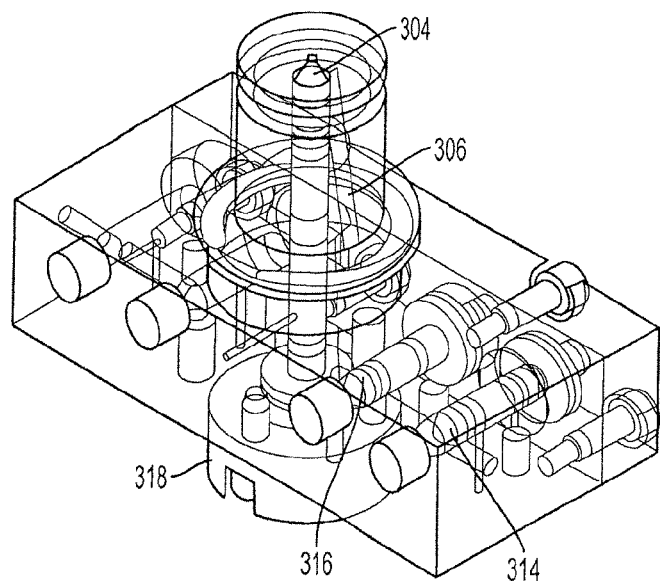
FIGS. 15A-15D illustrate various views of another embodiment of a system for obtaining samples from enclosed containers.
Figure 15B:
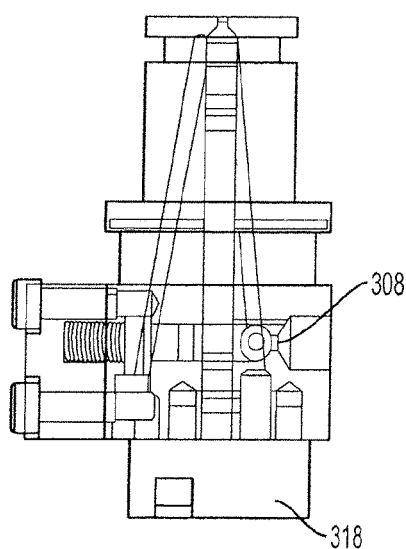
Figure 15C:
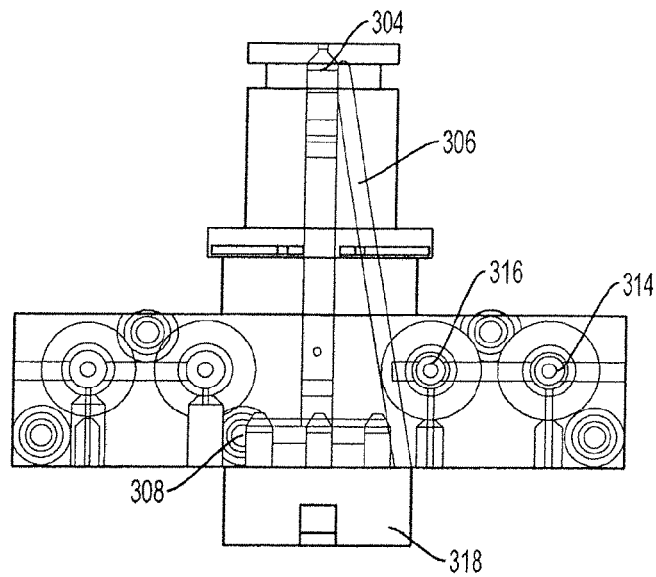
Figure 15D:
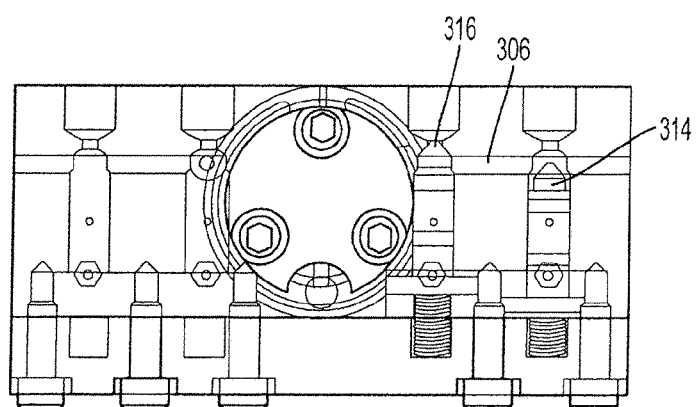

FIGS. 12-14 illustrate an embodiment of a control valve 136 that comprises a diaphragm valve. As shown in FIGS. 13 and 14, control valve 136 can comprise a diaphragm 191 positioned between two wall members 193, 195 to restrict and/or allow flow through the control valve. For example, first wall member 193 can comprise an inlet 196 and an outlet 197. Movement of diaphragm 191 towards first wall member 193 restricts passage of fluid through inlet 196 and outlet 197. To provide for movement of diaphragm 191, a control air inlet 199 can be provided on the opposing second wall member 195. An increase in air pressure at control air inlet 199 causes diaphragm 191 to move towards first wall member 193, while a decrease in air pressure at control air inlet 199 causes diaphragm 191 to move away from first wall member 193. In this manner, back pressure can be adjusted adjacent the outlet valve of the sampling system as needed or desired.

Referring again to FIG. 12, a holding coil 189 can be provided to contain a sample during a sample collection processing. Holding coil 189 can provide a volume into which a sample can be drawn. In operation, the sample is pumped or drawn into holding coil 189 and then drawn into the chamber from holding coil 189. This can allow larger samples to be drawn and, if the sample drawn is larger than the sample delivered into chamber 110, ensure that the sample delivered into chamber 110 is from a central region of the drawn sample. By capturing a central portion of the sample, the likelihood of that sample being contaminated within the flow path of the sampling system can be further reduced.

FIGS. 15A-15D illustrate various views of an integral sampling system 300. As in other embodiments, sampling system 300 includes a sample collection valve 304, an outlet valve 308, a sanitizing fluid inlet valve 314, a gas inlet valve 316, and a flow path 306 extending along these valves. A variable volume reservoir 318 can comprise a diaphragm pump that is configured to draw fluid from a bioreactor through an open sample collection valve 304. Sampling system 300 can be formed of an integral structure that can be coupled to a bioreactor to drawn samples therefrom.

As discussed above, the variable volume reservoirs can include a diaphragm pump or other similar structures. FIG. 16 illustrates a sampling apparatus 400 that comprises a variable volume reservoir 418. Sampling apparatus 400 can generally function similar to other sampling apparatuses described herein. However, instead of the diaphragm pumps illustrated in the other embodiments, variable volume reservoir 418 is a syringe-type pump. Thus, by operating the syringe-type pump to increase a volume in variable volume reservoir 418, the sample is drawn through open sample collection valve 404, into flow path 406, and into the reservoir of the syringe-type pump. As the volume in the syringe-type pump is decreased, the sample is discharged from the reservoir of the variable volume reservoir 418 and out the outlet valve 408.

The automated sampling systems described herein can advantageously allow for more frequent collection of data, reduce sampling variation and human error associated with the capturing of samples, and reduce costs by reducing labor requirements associated with manual sampling.

In one embodiment, the aseptic sample system extracts a sample from the vessel at least once in 8 hours, at least once in 6 hours, at least once in 4 hours, at least once in 2 hours, at least once in 1 hour, at least once in 0.5 hours, at least once every 20 minutes, at least once every 15 minutes, at least once every 10 minutes, and/or at least once every 5 minutes.

Exemplary Applications of Various Systems and Methods Disclosed Herein

As described herein, bioreactor feed strategies are typically developed over a series of experiments using limited empirical off-line data. Since cell physiology dynamically determines the nutrient requirements of the culture, obtaining the appropriate data over the appropriate time intervals with which to assess the behavior of the cell population to optimize the performance of the bioreactor process. The aseptic automatic bioreactor sampling systems and on-line dielectric spectroscopy measurements described herein, coupled with cell-based bioreactor models, can provide a less invasive monitoring and feedback system, and can be implemented through the use of customized bioreactor control code. Moreover, the systems and methods described herein can shorten development timelines and deliver higher quality process producing product with a significantly lower cost of goods.

As described in more detail herein, in some embodiments, novel bioreactor monitoring technologies can be applied to bioreactor processes and the resulting data can be interpreted into useful process understanding which can be leveraged for better control of the process.

The following example is described with reference to FIG. 2, which illustrates a schematic view of an embodiment of a novel system for providing online and at-line bioreactor monitoring and feedback tools for rapid process development.

Bioreactor System/Analytical Devices—Observability

In some embodiments, observability can be achieved by enhanced sampling (e.g., 10-15× over conventional manual sampling) coupled with measurements at deeper levels. For example, as shown in FIG. 2, additional at-line process analytical technologies can be employed to generate data which are data-rich and cell-level (as opposed to pH, DO, Temperature). This enhanced data package can provide the substrate for understanding the process from the base process levels that most directly affect the product.

Sufficient observability of the process can be achieved in various manners to facilitate the methods described herein. This observability can be achieved by process analytical technology (PAT) that provides 1) frequent enough data collection to create a robust model of the process, and 2) data from the levels of the process which are most directly affecting the product. Such PAT can include, for example, an automated aseptic sampling (AAS) valve, such as is described herein, and dielectric spectroscopy. The AAS valve can be used to generate more frequent data at-line and at production scale for cell culture processes.

The AAS valve can be a self-steam sterilizing auto-sampling valve, such as is described elsewhere herein, which can feed sample to at-line PAT at frequencies such as those described above. Depending on which at-line measurements are employed, the AAS valve can allow generation of media, cell, and product level information across scales.

Dielectric spectroscopy can be used to illuminate the cell-level behavior of the process. This non-invasive method can provide a data-rich cell-level snapshot of the cells in the bioreactor. Using dielectric spectroscopy, a probe can detect the capacitance, or ability to store electrical charge, of the cells in suspension as a function of frequency. The resulting capacitance, or dielectric spectrum will be affected by cell attributes like morphology, membrane charge, organelles, health, and buildup of key metabolites within the cell, and can therefore yield information about these attributes in real-time if analyzed correctly.

Process Understanding and Modeling

In some embodiments, process understanding and data analysis can include the application of key tools, models, flowcharts to reduce large data sets into useful guidance. The resulting data package can be analyzed in such a way as to create useful information and process understanding from the data. Tools such as multi-variate analysis (MVA), cell- and reactor-level modes, and creative experimentation can be used to greatly simplify the analysis of this data. The understanding generated from this type of analysis can result in something more like a product-scale model linking the process parameters, or inputs, to the observed product properties, or out puts, via the intermediate cell-level observations gained from the additional PAT. This model, representing an enhanced understanding, can then be leveraged to control the bioreactor process from a more product-level scope.

In order to turn the potentially daunting amount of data generated from the enhanced PAT employed, the novel systems and methods described herein can turn that data into useful guidance for process monitoring and development. For example, multi-variate data analysis (MVA) techniques, coupled with appropriate process models and subsequent experimentation, can greatly aid in the reduction of this data into useful process guidance. Some example tools which can be utilized include, for example, (1) computational fluid dynamic (CFD) models to answer key production scale vessel design questions such as vent filter placement to reduce fouling, sparge design, and mass transfer optimization, (2) impeller design guidance based upon bioreactor modeling (e.g., Matlab software-based and CFD commercial software-based) and appropriate experimental verification, (3) predictive cell-based models to address specific product-quality issues, (4) cell/tank modeling user interface based on kinetic and CFD modeling, (5) CFD modeling, (6) latent variable modeling (LVM), (7) transport/dimensional analysis, and (8) reaction kinetics.

Process Control

As shown in FIG. 2, process control strategies (e.g., as implemented by control software) can apply process understanding to transform the actual bioreactor process. Such strategies can provide improved active control and/or support for development of process strategy. Enhanced process understanding generated from this approach can be used to create additional "handles" with which to control the process from the cell level. For example, the feed rate of a component (e.g., nutrient or other feeds) can be modified according to the observed cell state, made possible by interpretation of cell-level data, as illustrated in FIG. 2.

Thus, using the systems described herein, a sample (e.g., a control volume) can be analyzed at both the macro level (e.g., fluid models and PATs that provide information about the impact of the reactor heterogeneity and operation) and micro level (e.g., fluid models and PATs that provide experimental data on rate-limiting steps that impact growth and productivity). For example, at the micro level, dielectric spectroscopy can be used to provide information about cell populations, individual cells, and organelles. In some embodiments, the size of the sample can be selected based on the smallest volume that contains all of the physics that the system is intended to measure.

The systems described herein result in improvements in at least one of bioproduct yield, bioproduct quality, bioproduct purity, bioproduct production rate, reduced cost, reduced energy consumption, and reduced waste generation, relative to a system that is controlled manually or in the absence of the system described herein.

Example 1

A system similar to that shown in FIG. 1 was used to demonstrate the utility of the invention. A bioreactor (3-L Broadley-James reactor vessel, Irvine, CA) was coupled to a Nova Bioprofile® FLEX online autosampler (Waltham, MA) to measure the concentration of glucose in the bioreactor. In response to the measured concentration of glucose, a control system was operably connected to a pump for adding glucose to the bioreactor.

The procedure used in this example was as follows. First, the bioreactor was charged with 2 L of media consisting of glucose and pH 7.4 phosphate buffered saline (PBS) (Sigma-Aldrich, Milwaukee, WI). The initial concentration of glucose in the bioreactor was about 1.3 g/L.

Glucose utilization in the bioreactor was simulated by diluting the contents of the bioreactor by adding 550 mL/hr of PBS. Samples from the bioreactor were analyzed every hour using the autosampler. The autosampler valve works by running a sanitizing solution through the lines, followed by a flush solution (available from Nova Biomedical). The sample is then collected, and sent to the analyzer for glucose analysis.

The system is also equipped with a control system that is operably connected to a pump for adding glucose to the bioreactor. Using the measured glucose concentration in the bioreactor, the control system operates a glucose pump that is connected to a glucose reservoir containing a concentration of 300 g/mL in PBS. The control system turns the pump off or on depending on the measured glucose concentration. In this example, the target glucose concentration was set at 1 g glucose/L in the bioreactor.

The results of Example 1 are presented in Table 1, which shows that sampling every hour allowed the system to achieve steady-state (±0.1 g/L of the set point) after about 4 hours of operation.

TABLE 1

Glucose Concentration versus Time for Example 1

| Time (hr) | Glucose Concentration (g/L) |
|---|---|
| 0 | 1.33 |
| 1 | 0.50 |
| 2 | 2.02 |
| 3 | 1.40 |
| 4 | 0.96 |
| 5 | 1.06 |
| 6 | 0.99 |
| 7 | 0.96 |
| 8 | 1.02 |
| 9 | 1.07 |
| 10 | 0.97 |
| 11 | 0.99 |
| 12 | 1.00 |
| 13 | 1.03 |

As a control, the system used in Example 1 was operated such that the sampling occurred once every 4 hours. In addition, the initial concentration of glucose in the bioreactor was 1.24 g/L. The results of these tests are shown in Table 2, which shows that it took at least 16 hours to achieve steady state operation.

TABLE 2

Glucose Concentration versus Time for Control 1

| Time (hr) | Glucose Concentration (g/L) |
|---|---|
| 0 | 1.24 |
| 4 | 0.91 |
| 8 | 0.71 |
| 12 | 1.28 |
| 16 | 0.96 |
| 20 | 1.00 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of making a bioproduct comprising:
    extracting a sample from a vessel containing whole broth that can produce the bioproduct, wherein the sample is extracted using an automated sampling system and the whole broth contains media and at least one undissolved species;
    delivering the sample to an analytical instrument;
    measuring at least one property of the whole broth in the sample with the analytical instrument;
    generating at least one first signal in response to the measured at least one property;
    generating at least one output signal that controls at least one device that is configured to alter at least one property of the whole broth within the vessel, the at least one output signal being generated in response to the at least one first signal; and
    altering the at least one property of the whole broth within the vessel by the at least one device;
    wherein the automated sampling system is operably connected to the vessel and capable of extracting the sample from the vessel at predetermined intervals, and
    wherein the undissolved species being selected from the group consisting of live cells, dead cells, cell fragments, solid substrates having cells adhered thereto, and mixtures thereof, wherein the automated sampling system comprises a variable volume reservoir that includes a reservoir, a reservoir inlet, and a reservoir outlet that is different from the reservoir inlet, and extracting the sample from the vessel comprises:
    delivering the sample into the reservoir through the reservoir inlet; and
    discharging the sample from the reservoir by reducing a volume of the reservoir to cause the sample to exit the reservoir through the reservoir outlet, wherein the variable volume reservoir comprises a movable member and a housing, the movable member being configured to move between a first position where the reservoir has a first volume to draw the sample into the reservoir through the reservoir inlet and a second position where the reservoir has a second, smaller volume to discharge the sample from the reservoir through the reservoir outlet.

2. The method of claim 1, wherein the variable volume reservoir is a flexible diaphragm.

3. The method of claim 1, wherein the variable volume reservoir is a syringe pump.

4. The method of claim 1, wherein the bioproduct is selected from the group consisting of foods, beverages, biofuels, bioenergy, bio-based ethanol, biodiesel, bio-based adhesives, biochemicals, biotherapeutics, biodegradable plastics, and mixtures thereof.

5. The method of claim 1, wherein the bioproduct is a biotherapeutic.

6. The method of claim 5, wherein the biotherapeutic is selected from the group consisting of pharmaceuticals, therapeutic proteins, protein fragments, antibodies, vaccines, and mixtures thereof.

7. The method of claim 1, wherein the vessel is selected from the group consisting of anaerobic fermenters, aerobic fermenters, stirred-tank reactors, adherent bioreactors, wave-type bioreactors, and disposable bioreactors.

8. The method of claim 1, wherein the undissolved species comprises one or more selected from the group consisting of bacteria, yeast, mammalian cells, and *e-coli* cells.

9. The method of claim 1, wherein the at least one property of the whole broth comprises media-level properties.

10. The method of claim 1, wherein the at least one property of the whole broth comprises cell-level properties.

11. The method of claim 1, wherein the at least one property of the whole broth is selected from the group consisting of pH, dissolved oxygen, osmolality, nutrient concentrations, ammonia/ammonium, lactate/lactic acid, pCO2, electrolytes (such as K+, Ca++, and/or Na+), amino acids, NAD/NADH, impurities, purity, phenotypes, metabolic states, cell health, cell cycle, cell state, cell number, and viable cell volume.

12. The method of claim 1, wherein the analytical instrument is selected from the group consisting of pH probes, dissolved oxygen meters, ion-selective electrodes, osmometry, high-performance liquid chromatography, ultra performance liquid chromatography, gas chromatography, ion chromatography, conductivity, Raman spectroscopy, near infrared spectroscopy, dielectric spectroscopy, fluorometry, ultraviolet/visible spectroscopy, capacitance probes, luminescence, redox probes, flow cytometry, hemacytometry, electro-rotation, electrophoresis, dielectrophoresis, and mixtures thereof.

13. The method of claim 1, wherein the device that alters the at least one property of the whole broth is selected from the group consisting of mixing/agitation systems, temperature-control systems, gas pumps, nutrient pumps, product removal systems, impurity removal systems, pH adjustment systems, and combinations thereof.

14. The method of claim 1, wherein the automated sampling system extracts a sample from the vessel at least once every 4 hours.

15. The method of claim 1, wherein the automated sampling system extracts a sample from the vessel at least once every 2 hours.

16. The method of claim 1, wherein the automated sampling system extracts a sample from the vessel at least once every 1 hour.

17. The method of claim 1, wherein the automated sampling system extracts a sample from the vessel at least once every 0.5 hours.

18. The method of claim 1, wherein altering the at least one property of the whole broth within the vessel results in an improvement in at least one of bioproduct yield, bioproduct quality, bioproduct purity, and bioproduct production rate.

* * * * *